(12) United States Patent
Shin

(10) Patent No.: US 6,380,383 B1
(45) Date of Patent: Apr. 30, 2002

(54) COMPOUND FOR THE ALUMINUM FILM FROM CHEMICAL VAPOR DEPOSITION AND THE METHOD OF SYNTHESIS

(75) Inventor: Hyun-Koock Shin, Kyungki-Do (KR)

(73) Assignee: Rohm and Haas Company, Philadelphia, PA (US)

(*) Notice: Subject to any disclaimer, the term of this patent is extended or adjusted under 35 U.S.C. 154(b) by 0 days.

(21) Appl. No.: 09/595,109

(22) Filed: Jun. 16, 2000

Related U.S. Application Data

(62) Division of application No. 09/283,317, filed on Mar. 31, 1999, now Pat. No. 6,121,443.

(30) Foreign Application Priority Data

Sep. 15, 1998 (KR) .............................. 98-38572

(51) Int. Cl.$^7$ .................... C07D 207/00; C07D 333/46; B05D 5/12
(52) U.S. Cl. ........................... 544/64; 544/225; 546/11; 548/402; 549/3; 549/206; 427/126.1; 427/250
(58) Field of Search ..................... 544/64, 225; 546/11; 548/402; 549/3, 206; 427/126.1, 250

(56) References Cited

U.S. PATENT DOCUMENTS

| | | | |
|---|---|---|---|
| 4,473,743 A | 10/1984 | Marlett | |
| 4,923,717 A | 5/1990 | Gladfelter et al. | 427/252 |
| 5,113,025 A | 5/1992 | Park et al. | |
| 5,136,046 A | 8/1992 | Park et al. | |
| 5,178,911 A | 1/1993 | Gordon et al. | 427/255 |
| 5,180,687 A | 1/1993 | Mikoshiba et al. | 437/187 |
| 5,191,099 A | 3/1993 | Gladfelter et al. | 556/27 |
| 5,330,633 A | 7/1994 | Matsumoto et al. | 204/298 |
| 5,393,699 A | 2/1995 | Miksoshiba et al. | 437/187 |
| 5,900,279 A | 5/1999 | Hideaki et al. | |

FOREIGN PATENT DOCUMENTS

FR    1245361    1/1960

OTHER PUBLICATIONS

Atwood et al., Inorg. Chem. vol. 32, No. 16, pp. 3482–3487, 1993.*
"Reactions of Lithium Aluminum Hydride with Representative Elements of the Main Groups of the Periodic System" by Thomas Wartik and H. I. Schlesinger, J. Am. Chem. Soc. vol. 75, pp. 835–839, 1953.
Greenwood et al., "Investigation of the Properties and Thermochemistry of Some Complexes of Aluminum Hydride with Tertiary Amines and Diamines", J. Chem. Soc. (A), 1971 pp. 814–817.
Yoon et al., "Mechanism of Aldehyde Synthesis from Ester by Sodium Diethylpiperidinohydroaluminate", Bull. Korean Chem. Soc. vol. 13, No. 3, 1992, pp. 339–341.
Yoon et al., "Sodium Diethylpiperidinohydroaluminate, a New Selective Reducing Agent", J. Org. Chem. 1993, pp. 1941–1944.
Yoon, "Selective Reduction of Organic Compounds with Aluminum and Boron Hydrides", Pure & Appl. Chem., vol. 68, No. 4, pp. 843–848, 1996.
Fuller et al., "Lithium Aluminum Hydride–N–Methylpyrrolidine Complex 1. Synthesis and Reactivity of Lithium Aluminum Hydride–N–Methylpyrrolidine Complex. An Air and Thermally Stable Reducing Agent Derived from Lithium Aluminum Hydride", Tetrahedron Letters, The International Journal of the Rapid Publication of Preliminary Communications in Organic Chemistry, pp. 1515–1518.
Marlett et al., "Dimethylethylamine–Alane and N–Methylpyrrolidine–Alane. A Convenient Synthesis of Alane, a Useful Selective Reducing Agent in Organic Synthesis", J. Org. Chem. 1990, 55, 2968–2969.
Thiele et al., "Electron donor–acceptor complexes of aluminum trialkyls with bivalent Lewis bases. II. Complexes of Trimethylaluminum with heterocyclic bidentate ligands", Z. Anorg. Allg. Chem. No. 3–4, 1996, pp. 179–188.
Sen et al., "Monomeric and dimeric complexes of Group IIIA metal alkyls with piperidine. Effect of coordination on the carbon–metal bond", J. Inorg. Nucl. Chem., vol. 15, No. 9, 1976, pp. 2207–2215.
Beachley, O.T., Jr. et al., "Chelation in 1–5 organoaluminum–nitrogen chemistry" Inorg. Chem., vol. 15, No. 9, 1976, pp. 2207–2215.
Watkins et al., "27Al and 13C NMR Relaxation Studies in Aminoalanese", Inorg Chem., vol. 34, No. 24, 1995, pp. 6228–6230.
Styron, Eric K. et al., "Reactivity of Triethylaluminum with a series of secondary amines. Aduct and aminoalane dimer synthesis and characterization; the crystal structure os Et2AlN(c–CgH11) 2 2 and Et2AlNCH3 2", Polyhedron (1999); 18(11), 1595–1602.
Henrickson et al., "Lewis acidity of alanes. Interactions of trimethylalane with sulfides"Inorg. Chem., vol. 6, No. 8, 1967, pp. 1461–1465.
Thomas, C. J. et al., "Reactivity of bis(trimethylaluminum) with selected aminoarsines and secondary amines"Polyhedron, vol. 12, No. 4, 1993, pp. 389–399.

\* cited by examiner

*Primary Examiner*—T. A. Solola
(74) *Attorney, Agent, or Firm*—S. Matthew Cairns

(57) ABSTRACT

Organometallic precursor compounds useful for forming aluminum films by chemical vapor deposition are disclosed. Also disclosed are methods of preparing the organometallic precursor compounds and methods of forming aluminum films.

6 Claims, No Drawings

COMPOUND FOR THE ALUMINUM FILM FROM CHEMICAL VAPOR DEPOSITION AND THE METHOD OF SYNTHESIS

This application is a div of Ser. No. 09/283,317 filed Mar. 31, 1999 now U.S. Pat. No. 6,121,443.

BACKGROUND OF THE INVENTION

This invention generally relates to compounds used for the chemical vapor deposition of metal films. In particular, this invention relates to precursor compounds for use in the chemical vapor deposition of aluminum films.

In the semiconductor industry, technological and material development have resulted in the miniaturization, high reliability, high speed, high functionality, and high degree of integration of devices, such as semiconductor integrated circuits. With the development of the manufacturing process of semiconductor devices, the development of improved memory devices, such as dynamic random access memory ("DRAM"), has been rapid. Currently, 64 mega DRAM is under mass production and, in the year 2,000, it is anticipated that with the new manufacturing methods of the next generation semiconductor devices, as well as with their mass production capabilities, 256 mega class memory devices may be available, as well as 1 giga ("G") and 4 G class high memory devices.

The next generation memory devices, those having high memory capacity, are the result of miniaturization of the memory device circuits; specifically, narrowing the line widths to 0.25, 0.18, and 0.15 microns ("$\mu$m").

The current wiring method in the semiconductor memory devices using aluminum as the wiring material is by vapor deposition, i.e., the sputtering method in which a metal, i.e. aluminum, itself is used for deposition to attain a desired thin film. This method limits the manufacturing process technology in achieving the narrowing of the line width described above.

In the manufacturing of 64 mega DRAM using aluminum (Al) metal wiring, the sputtering method has been the sole method used in the deposition of aluminum from an aluminum target. In the next generation memory devices described above, the circuit line width would be less than 0.25 $\mu$m and the aspect ratio (depth/diameter) of contact and via hole is large in the vapor deposited metal, thus, the use of sputtering in the vapor deposition process would be unsuitable.

To alleviate such a problem, an aluminum wiring process using chemical vapor deposition ("CVD") method has been studied for a long time. This method has a high step coverage and has an improved burying process of contact/via hole, which is an advantage of the method. Thus, aluminum wiring from vapor deposition of aluminum ("Al-CVD" or aluminum chemical vapor deposition) will be the foundation of the technology for the production of the next generation class memory devices and the CVD method is considered to be the imperative method.

In aluminum film deposition using the chemical vapor deposition method, an aluminum compound, known as the precursor, was used as the source material. The chemical properties and the selection of the compound greatly affect the CVD process and they are the most important elements in the process. Therefore, prior to the selection of the deposition method, it is imperative that the selection and development of the precursor are the first factors to be considered.

In spite of the importance of the role of a precursor, the metal film deposition process using CVD method has developed concurrently with the use of the process in the manufacture of the next generation semiconductor devices. For this reason the development of the precursors for Al-CVD has been delayed.

In the early stage of Al-CVD method development, alkyl aluminum compounds were widely used in the industry. The typical alkyl aluminum compounds commonly used were trimethylaluminum, as represented by the chemical formula of Al(CH$_3$)$_3$, and triisobutylaluminum, as represented by the chemical. formula of [(CH$_3$)$_3$CHCH$_2$]$_3$Al.

In the nineteen-nineties, the development of precursors for aluminum film deposition using the chemical vapor deposition process was very active in Japan resulting in the development of dimethylaluminum hydride, represented by the chemical formula of [(CH$_3$)$_2$AlH]$_2$, and in the USA resulting in the development of dimethylethylaminealane, represented by the chemical formula of H$_3$Al:N(CH$_3$)$_2$C$_2$H$_3$. These compounds were leading precursors in the Al-CVD process.

Among the chemical compounds examined, dimethylethylaminealane was synthesized by Wayne Gladfelter of the University of Minnesota, in 1989, after the report of J. K. Ruff et al. in the Journal of the American Chemical Society, 1960. The synthesis of dimethylethylamine, (N(CH$_3$)$_2$C$_2$H$_3$) has not been reported in the complex compound developed from aluminum hydride (AlH$_3$) and an alkyl amine in the report. U.S. Pat. No. 5,191,099 (Gladfelter et al.) discloses dimethylethylaminealane as a precursor in Al-CVD process.

Other chemicals, such as dimethylaluminum hydride, trimethylaluminum, and triisobutylaluminum, have been developed and have been used widely in various applications since the nineteen-fifties. Specifically, dimethylaluminum hydride was reported by T. Wartik et al., Journal of American Chemical Society, 1953, 75, 835, and trimethylaluminum and triisobutylaluminum have been reported quite a bit earlier than the above.

These compounds have been fully commercialized and used in many industrial areas prior to the nineteen-nineties. They can be obtained economically, and they are liquid at room temperature, which are their advantages. However, the above-mentioned compounds have some problems when used as the precursors in the Al-CVD process. The film deposition temperature is above 300° C. and near 400° C. Due to this high deposition temperature, the vapor deposition process becomes very difficult and the high temperature deposition results in the inclusion of carbon impurities which increase the electric resistance of the deposited film, which are the detrimental flaws.

To alleviate such problems in the Al-CVD process, a dimethylaluminum hydride precursor and related technologies were developed in the early part of the nineteen-eighties. Dimethylaluminum hydride has a high vapor pressure (2 torr at 25° C.) and its vapor deposition rate is high and it is a colorless liquid compound at room temperature. Also, advantageously, it provides very pure aluminum film that can be deposited at a low temperature (30° C.) when hydrogen gas is used as the reaction gas. However, dimethylaluminum hydride is an alkylaluminum compound that explodes when it comes into contact with air. Therefore, it is very difficult to handle and has high degree of difficulty in the manufacturing process which results in a low yield and high cost.

As alternative precursors in the Al-CVD process, the alane (AlH$_3$) derivatives were used besides dimethylaluminum hydride. One of the alane derivatives, dimethylethylaminealane, forms a vapor deposition film of high purity at low temperature, 100–200° C. Dimethylethylaminealane is a colorless chemical compound at room temperature and has a relatively high vapor pressure (1.5 torr at 25° C.). In comparison with dimethylaluminum hydride, the flammability is somewhat less and it can be manufactured by a comparatively simple process at a low cost, which is advantageous.

However, dimethylethylaminealane is thermally unstable at room temperature as well as during the vapor deposition process, which is carried out at 30° to 40° C. Hence, during storage the precursor gradually decomposes in the container. This difficulty in room temperature storage is a disadvantage. For this reason, development and reproducibility of the vapor chemical deposition process has been difficult in semiconductor device manufacturing processes.

SUMMARY OF THE INVENTION

It has now been found that certain aluminum compounds retain the advantages of known precursors for aluminum film deposition and solve the problems of these known precursors for Al-CVD applications.

The present invention provides an organometallic compound of the formula $$H(R')_2Al:L_n \quad (I)$$

wherein R' is an alkyl or perfluoroalkyl group having 1 to 4 carbons; and L is one or more Lewis bases capable of providing an unshared electron pair to the aluminum and is selected from thiophene, thiopyran or an organic amine of formula II or III

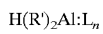

(II)

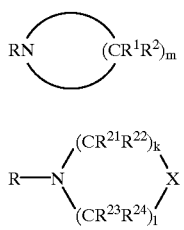

(III)

wherein R is an alkyl having a carbon number of 1 to 4; $R^1$, $R^2$, $R^{21}$, $R^{22}$, $R^{23}$ and $R^{24}$ are each independently hydrogen (H) or an alkyl group having carbon numbers of 1 to 2; X is oxygen or an alkyl group containing nitrogen; m is an integer from 2 to 8; k and l are each independently integers from 1 to 3; and n is 1 or 2.

The present invention also provides a vapor deposition precursor composition comprising an organometallic compound described above.

The present invention also provides a process for aluminum film formation comprising the step of vapor depositing an aluminum film on a substrate, wherein the source of aluminum in the aluminum film is a vapor deposition precursor comprising an organometallic compound of the formula $H(R')_2Al:L_n$; wherein R' is an alkyl or perfluoroalkyl group having 1 to 4 carbons; and L is a Lewis base capable of providing an unshared electron pair to the aluminum and is selected from thiophene, thiopyran or an organic amine of formula II or III

(II)

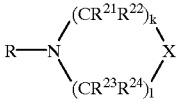

(III)

wherein R is an alkyl having a carbon number of 1 to 4; $R^1$, $R^2$, $R^{21}$, $R^{22}$, $R^{23}$ and $R^{24}$ are each independently hydrogen (H) or an alkyl group having carbon numbers of 1 to 2; X is oxygen or an alkyl group containing nitrogen; m is an integer from 2 to 8; k and l are each independently integers from 1 to 3; and n is 1 or 2.

The present invention further provides a process for preparing an organometallic compound of the formula $H(R')_2Al:L_n$; wherein R' is an alkyl or perfluoroalkyl group having 1 to 4 carbons; and L is one or more Lewis bases capable of providing an unshared electron pair to the aluminum and is selected from thiophene, thiopyran or an organic amine of formula II or III

(II)

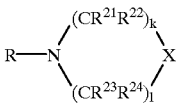

(III)

wherein R is an alkyl having a carbon number from 1 to 4; $R^1$, $R^2$, $R^{21}$, $R^{22}$, $R^{23}$ and $R^{24}$ are each independently hydrogen (H) or an alkyl group having carbon numbers of 1 to 2; X is oxygen or an alkyl group containing nitrogen; m is an integer from 2 to 8; k and l are each independently integers from 1 to 3; and n is 1 or 2, comprising the steps of: a) forming a suspension of trialkylaluminum of the formula $R'_3Al$ wherein R' is as defined above and lithium aluminum hydride in hexane or pentane; and b) adding to the suspension said Lewis base.

DETAILED DESCRIPTION OF THE INVENTION

This invention pertains to organometallic compounds useful as precursors in the vapor deposition of aluminum film as wiring on semiconductor devices and methods of preparing the precursor compounds. Specifically, the precursors are useful in the formation of an aluminum metal film layer on a diffusion barrier layer or adhesion layer on a silicon substrate.

Lewis bases capable of providing an unshared electron pair to the aluminum metal center are useful in the present invention Suitable Lewis bases include thiophene, thiopyran, and organic amine derivatives of Formula II or Formula III. For example, the organic amine derivatives include one or more heterocyclic amines selected from alkylaziridine, alkylazetidine, alkylpyrrolidine, alkylpiperidine, alkylhexamethyleneimine, alkylheptamethyleneimine, alkylmorpholine, 1,4-dialkylpiperazine.

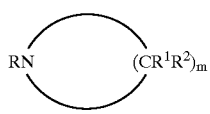
(II)

In the above Formula II, R is an alkyl having a carbon number of 1 to 4, $R^1$ and $R^2$ are each independently hydrogen (H) or an alkyl group having carbon numbers of 1 to 2, and m is an integer from 2 to 8. It is preferred that R is methyl or ethyl.

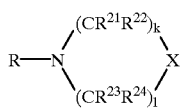
(III)

In the above Formula III, R is an alkyl group having carbon numbers of 1 to 4, $R^{21}$, $R^{22}$, $R^{23}$ and $R^{24}$ are each independently hydrogen (H) or alkyl group having a carbon number of 1 to 2, X is oxygen or an alkyl group containing nitrogen, and k and l are each independently integers of 1 to 3.

Among the compounds expressed by Formula II, the preferred compounds are alkylaziridines having Formula IV, alkylpyrrolidines having Formula V and alkylpiperidines having Formula VI. Among the compounds expressed by Formula III, the preferred compounds are alkylmorpholines having Formula VII and alkylpiperazines having Formula VIII.

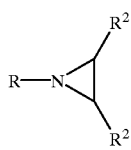
(IV)

In the above Formula IV, it is preferred that R is methyl or ethyl and $R^2$ is hydrogen or methyl. It is more preferred that R and $R^2$ are both methyl.

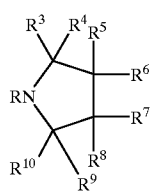
(V)

In the above Formula V, R is an alkyl group having a carbon number of 1 to 4, and $R^3$ to $R^{10}$ are each independently hydrogen or alkyl group having a carbon number of 1 to 2. Preferred compounds of Formula V are those wherein $R^3$, $R^4$, $R^6$, $R^7$, $R^9$ and $R^{10}$ are each independently hydrogen or methyl, more preferably wherein $R^5$ and $R^8$ are hydrogen, and most preferably wherein R is methyl, ethyl or butyl. 1-Methylpyrrolidine and 1,4-dimethylpyrrolidine are particularly preferred.

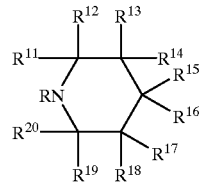
(VI)

In the above Formula VI, R is an alkyl group having a carbon number of 1 to 4, and $R^{11}$ to $R^{20}$ are each independently hydrogen or an alkyl group having a carbon number of 1 to 2. Preferred compounds of Formula VI are those wherein R is methyl or ethyl, and $R^{11}$, $R^{12}$, $R^{14}$, $R^{16}$, $R^{18}$, $R^{19}$ and $R^{20}$ are each independently hydrogen or methyl. 1-Methylpiperidine, 1-ethylpiperidine and 1,2,2,6,6-pentamethylpiperidine are particularly preferred.

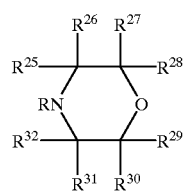
(VII)

In the above Formula VII, R is an alkyl group having a carbon number of 1 to 4, and $R^{25}$ to $R^{32}$ are each independently hydrogen or an alkyl group having a carbon number of 1 to 2. Preferred compounds of Formula VII are those wherein R is methyl or ethyl and $R^{25}$, $R^{26}$, $R^{27}$, $R^{28}$, $R^{29}$, $R^{30}$, $R^{31}$ and $R^{32}$ are each independently hydrogen or methyl. 4-Ethylmorpholine is particularly preferred.

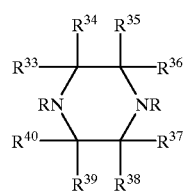
(VIII)

In the above Formula VIII, R is an alkyl group having a carbon number of 1 to 4, and $R^{33}$ to $R^{40}$ are each independently hydrogen or an alkyl group having a carbon number of 1 to 2. Preferred compounds of Formula VIII are those wherein R is methyl or ethyl and $R^{33}$, $R^{34}$, $R^{35}$, $R^{36}$, $R^{37}$, $R^{38}$, $R^{39}$ and $R^{40}$ are each independently hydrogen or methyl. It is more preferred that R is methyl and $R^{33}$, $R^{34}$, $R^{35}$, $R^{36}$, $R^{37}$, $R^{38}$, $R^{39}$ and $R^{40}$ are each hydrogen.

Among the compounds defined by Formula II are those wherein the Lewis base is an alkylpyrrolidine. The preferred alkylpyrrolidine is defined by Formula IX. The preferred compounds of Formula IX are those wherein $R^3$, $R^4$, $R^6$, $R^7$, $R^9$ and $R^{10}$ are each independently hydrogen or methyl. The compounds defined by Formula IX include: 1,2-dimethylpyrrolidine having Formula X, 1-methylpyrrolidine having Formula XI, and 1-butylpyrrolidine having Formula XII. Among the compounds defined by Formula II are those wherein the Lewis base is an alkylpiperidine, having Formula VI, and preferably an alkylpiperidine having Formula XIII. It is more preferred that the alkylpiperidine is 1,2,2, 6,6-pentamethylpiperidine having Formula XIV, 1-methylpiperidine having Formula XV, and 1-ethylpiperidine having Formula XVI.

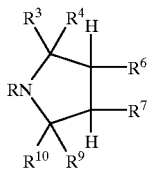

(IX)

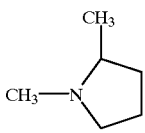

(XI)

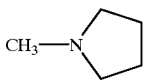

(XII)

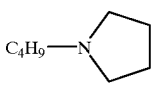

(XIII)

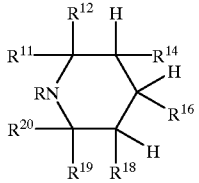

(XIV)

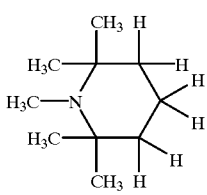

(XV)

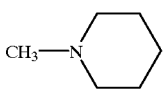

(XVI)

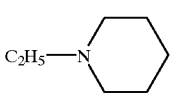

Among the compound defined by Formula III are those wherein the Lewis base is an alkylmorpholine shown by Formula VII. The preferred compounds defined by Formula VII include: 4-methylmorpholine having Formula XVII and 4-ethylmorpholine having Formula XVIII. Additionally, among alkylpiperazines having Formula VIII, the preferred one is 1,4-dimethylpiperazine, shown by Formula XIX.

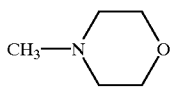

(XVII)

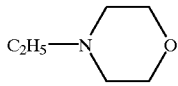

(XVIII)

(XIX)

Thus, the preferred organic amines are 1,2-dimethylpyrrolidine, 1-methylpyrrolidine, 1-butylpyrrolidine, 1,4-dimethylpyrrolidine, 1-methylpiperidine, 1-ethylpiperidine, 1,2,2,6,6-pentamethylpiperidine, 4-methylmorpholine, 4-ethylmorpholine and 1,4-dimethylpiperazine.

An aluminum compound represented by Formula I used for aluminum film vapor deposition can be readily prepared according to the chemical reaction represented by Equation 1. Hexane or pentane was added to a mixture of trialkylaluminum (Al(R')$_3$), and lithium aluminum hydride (LiAlH$_4$) in a reactor at room temperature to form a suspension and then a Lewis base, L, such as alkylpyrrolidine, alkylpiperidine, alkylmorpholine and alkylpiperazine, was added to obtain the compounds of the present invention.

$$LiAlH_4 + Al(R')_3 + nL \rightarrow H(R')_2Al: L_n + LiAlH_3(R') \quad \text{Equation 1}$$

In the above Equation 1, R' is an alkyl or perfluoroalkyl group with from 1 to 4 carbons, L is a Lewis base, and n is 1 or 2, as defined in Formula I. It is preferred that R' is methyl.

Among the Lewis base compounds useful in the present invention, the preferred are 1-methylpyrrolidine and 1-ethylpiperidine. Thus, the typical precursors for the vapor deposition of aluminum film as wiring material in semiconductor device manufacture are the compounds represented by Formula XX, which is 1-methylpyrrolidinedimethylaluminum hydride, and Formula XXI, which is 1-ethylpiperidinedimethylaluminum hydride. The invention will be discussed in relation to these two compounds, namely the use of these compounds as precursors in aluminum film vapor deposition.

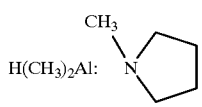

(XX)

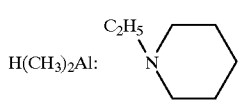

(XXI)

Dimethylaluminum hydride is well known as a precursor in aluminum film vapor deposition, and has been in use since the nineteen-eighties. However, a problem with this compound is its high viscosity and solving this viscosity problem will provide control in attaining a proper delivery rate when a bubbler or other liquid delivery system is used as the transporting system. The ease of the delivery rate control is very important in semiconductor device manufacture. Also important is the reproducibility in the aluminum film vapor deposition process, and such reproducibility allows for the development of aluminum vapor deposition process.

Conventional aluminum chemical vapor deposition ("CVD") precursor compounds, such as dimethylethylaminealane, trimethylaluminum and dimethylaluminum hydride, etc., ignite explosively when they contact water or air. The invention compounds are flammable but they do not ignite explosively or they are less flammable than the conventional precursors, so the risks of fire and personal injury are reduced.

The process of manufacturing the compounds can be carried out with ease and without any danger, yet the yield is high when compared with the manufacturing process of dimethylaluminum hydride. Moreover, the unit production cost will be less than that of dimethylaluminum hydride. Thus, it is expected that the compounds of the present invention would be excellent precursors in aluminum film vapor deposition by using chemical vapor deposition process.

The invention compounds are a liquid at room temperature, and thus, the control of the precursor compound delivery rate, which is closely related to process reproducibility, is easily achieved in the vapor deposition process by using a bubbler. Also, in other chemical vapor deposition processes that use a direct liquid injector or a liquid delivery system, the process can be easily carried out, which is an advantage. In a chemical vapor deposition process, the compounds of the present invention may be vaporized by thermal energy, plasma or a bias applied on the substrate.

Furthermore, as an added feature, the inventors developed precursor compound solutions which are more beneficial than known precursor solutions used in delivery systems such as direct liquid injectors and liquid delivery systems. A heterocyclic amine was used as the solvent for the preparation of a precursor solution for the delivery of the precursor compounds of Formula I, the solute, in a delivery system. Examples of the heterocyclic amine solvent include 1-methylpyrrolidine, 1-butylpyrrolidine, 1-methylpiperidine, 1-ethylpiperidine, 4-methylmorpholine, 4-ethylmorpholine, 1,4-dimethylpiperazine, and the like. It is preferred that the solvent is 1-methylpyrrolidine. The solutes and the solvents are used in various combinations, and the resulting aluminum compound solutions can be used as effective precursors in aluminum vapor deposition processes.

In aluminum film vapor deposition, the invention solutions allow for the development of new processes when compared with that of conventional precursor solutions due to the wide selection of precursors.

Solutions of the above new compounds represented by Formula I were prepared using a heterocyclic amine as the solvent. The new precursor compound solution can be prepared by dissolving the invention compound represented by Formula I in a heterocyclic amine which is free of water, a purified solvent, and a Lewis base. The entire reaction is carried out under an inert gas atmosphere, such as a nitrogen or argon stream, to prevent the deterioration of the compound due to exposure to air.

The invention compounds and the preparation of solutions of the compound will be discussed with examples.

EXAMPLE 1

Synthesis of 1-Methylpyrrolidinedimethylaluminum hydride

To a stirred, powder suspension of 198 g (2 moles) of trimethylaluminum and 95 g (2 moles) of lithium aluminum hydride in pentane under nitrogen stream at room temperature were added dropwise 212 g (2.5 moles) of colorless 1-methylpyrrolidine. The heat of the reaction was minute and it was not necessary to cool the reactor. The heat may have aided the reaction. Following the addition of 1-methylpyrrolidine, the reaction was allowed to stir for about 5 hours at room temperature.

After the completion of the reaction, the invention compound, which is 1-methylpyrrolidinedimethylaluminum hydride, was separated from the reaction mixture by filtration under a nitrogen stream to obtain a colorless, first filtrate. The byproducts on the filter were rinsed twice with a sufficient quantity of pentane, and then the rinsing solutions were added to the first filtrate. All of the volatile components in the filtrate were removed under vacuum at room temperature to obtain a colorless liquid.

The dried colorless filtrate was distilled at 45° C. under vacuum ($10^{-2}$ torr) and the distillate was condensed in a receiver chilled with dry ice. The colorless first distillate was processed in a similar manner at 40° C. to purify and to obtain 250 g of high purity 1-methylpyrrolidinedimethylaluminum hydride.

The reaction shown in Equation 2 is the preparation of 1-methylpyrrolidinedimethylaluminum hydride, and the highly purified 1-methylpyrrolidinedimethylaluminum hydride was analyzed by proton nuclear magnetic resonance (NMR), and the data and properties are listed in Table 1.

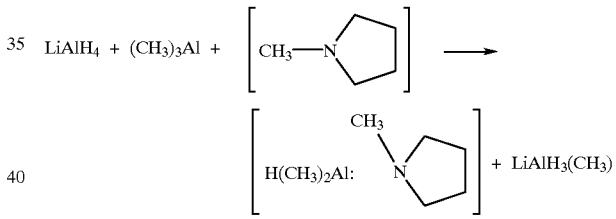

Equation 2

EXAMPLE 2

Synthesis of 1-Butylpyrrolidine

To a suspension of trimethylaluminum and lithium aluminum hydride in pentane prepared according to the procedure of Example 1, 279 g (2.2 moles) of 1-butylpyrrolidine were added dropwise at room temperature under a nitrogen stream and the mixture was stirred for 5 hours while heating. After filtration according to Example 1, the resulting filtrate was dried to obtain a colorless liquid.

The dried colorless liquid compound was distilled at 50° C. under vacuum ($10^{-2}$ torr), and collected in a receiver chilled with dry ice ($-78°$ C.) to obtain colorless, high purity 1-butylpyrrolidinedimethylaluminum hydride (332 g).

The reaction shown in Equation 3 is the preparation of 1-butylpyrrolidinedimethylaluminum hydride, and the compound was analyzed by proton nuclear magnetic resonance. The data and the observed properties are listed in Table 1. The results confirmed the compound as 1-butylpyrrolidinedimethylaluminum hydride.

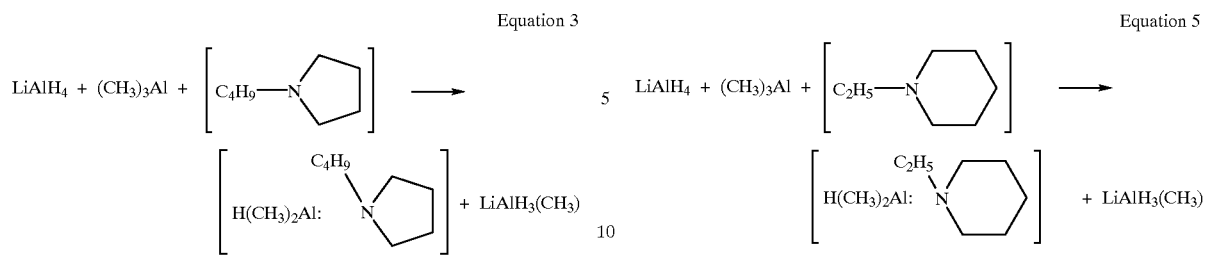

Equation 3

Equation 5

EXAMPLE 3

Synthesis of 1-Methylpiperidinedimethylaluminum hydride

To a suspension of trimethylaluminum and lithium aluminum hydride in pentane according to the procedure of Example 1, 218 g (2.2 moles) of 1-methylpiperidine were added dropwise at room temperature under a nitrogen stream, and the reaction mixture was stirred for 5 hours. After filtration according to Example 1, the colorless filtrate was dried under vacuum to obtain a colorless liquid.

The dried colorless liquid compound was distilled at 45° C. under vacuum ($10^{-2}$ torr) and the distillate was collected in receiver chilled with dry ice (−78° C.) to obtain 280 g of colorless, high purity 1-methylpiperidinedimethylaluminum hydride.

The reaction shown in Equation 4 is the preparation of 1-methylpiperidinedimethylaluminum hydride, and the product compound was analyzed by proton nuclear magnetic resonance. The data and the observed properties are listed in Table 1 and the product was confirmed as 1-methylpiperidinedimethylaluminum hydride.

EXAMPLE 5

Synthesis of 4-Ethylmorpholinedimethylaluminum hydride

To a suspension of trimethylaluminum and lithium aluminum hydride in pentane prepared according to the procedure of Example 1, 253 g (2.2 moles) of 4-ethylmorpholine were added dropwise at room temperature under a nitrogen stream and the reaction was carried out according to Example 1. After the completion of the reaction, the reaction product obtained by the procedure of Example 1 was separated to obtain 310 g of 4-ethylmorpholinedimethylaluminum hydride.

The reaction shown in Equation 6 is the preparation of 4-ethylmorpholinedimethylaluminum hydride, and the product compound was analyzed by proton nuclear magnetic resonance. The data and the observed properties are listed in Table I and the product was confirmed as 4-ethylmorpholinedimethylaluminum hydride.

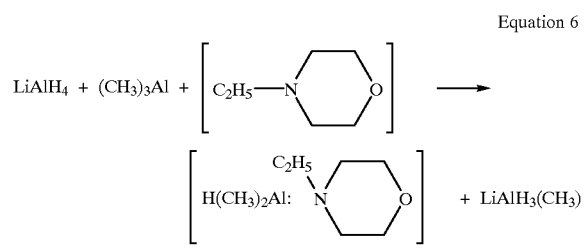

Equation 6

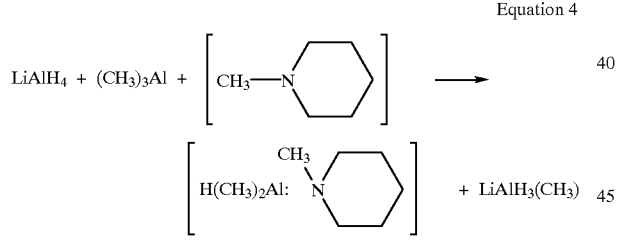

Equation 4

EXAMPLE 4

Synthesis of 1-Ethylpiperidinedimethylaluminum hydride

To a suspension of trimethylaluminum and lithium aluminum hydride in hexane prepared according to the procedure of Example 1, 249 g (2.2 moles) of 1-ethylpiperidine were added dropwise at room temperature under a nitrogen stream and the reaction was carried out according to Example 1. The product was filtered, dried, and distilled to obtain 308 g of colorless high purity 1-ethylpiperidinedimethylaluminum hydride.

The reaction shown in Equation 5 is the preparation of 1-ethylpiperidinedimethylaluminum hydride, and the product compound was analyzed by proton nuclear magnetic resonance. The data and the observed properties are listed in Table 1, and the product was confirmed as 1-ethylpiperidinedimethylaluminum hydride.

EXAMPLE 6

Synthesis of 1,4-Dimethylpiperazinedimethylaluminum hydride

To a suspension of trimethylaluminum and lithium aluminum hydride in pentane prepared according to the procedure of Example 1, 250 g (2.2 moles) of 1,4-dimethylpiperazine were added dropwise at room temperature under a nitrogen stream and the reaction was carried out according to Example 1. After the completion of the reaction, the reaction product obtained by the procedure of Example 1 was separated to obtain 260 g of 1,4-dimethylpiperazinedimethylaluminum) hydride.

The reaction shown in Equation 7 is the preparation of 1,4-dimethylpiperazinedimethylaluminum hydride, and the product compound was analyzed by proton nuclear magnetic resonance. The data and the observed properties are listed in Table 1, and the product was confirmed as 1,4-dimethylpiperazinedimethylaluminum hydride.

Equation 7

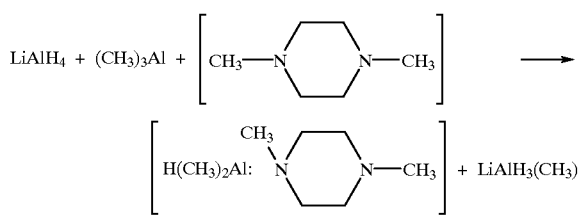

TABLE 1

| Example | Compound | Phase (20° C.) | Color | NMR Analysis (C$_6$D$_6$, ppm) |
|---|---|---|---|---|
| 1 | 1-Methylpyrrolidinedimethyl-aluminum hydride | liquid | colorless | δ −0.55 (s, 3H)<br>δ −0.50 (s, 3H)<br>δ −0.40 (s, 1H)<br>δ 1.30 (m, 4H)<br>δ 1.85 (s, 3H)<br>δ 2.40 (br, 4H)<br>δ 4.10 (br) |
| 2 | 1-Butylpyrrolidinedimethyl-aluminum hydride | liquid | colorless | δ −0.45 (s, 3H)<br>δ −0.38 (s, 3H)<br>δ −0.33 (s, 1H)<br>δ 0.78 (t, 3H)<br>δ 1.00 (m, 2H)<br>δ 1.38 (br, 6H)<br>δ 2.28 (t, 2H)<br>δ 2.45 (br, 4H)<br>δ 4.10 (br) |
| 3 | 1-Methylpiperidinedimethyl-aluminum hydride | liquid | colorless | δ −0.60 (s, 3H)<br>δ −0.55 (s, 3H)<br>δ −0.45 (s)<br>δ 1.05 (br, 2H)<br>δ 1.20 (br, 4H)<br>δ 1.95 (s, 3H)<br>δ 2.38 (br, 4H)<br>δ 4.05 (br) |
| 4 | 4-Ethylpiperidinedimethyl-aluminum hydride | liquid | colorless | δ −0.42 (s, 6H)<br>δ 0.85 (t, 3H)<br>δ 1.05 (br, 2H)<br>δ 1.15 (br, 4H)<br>δ 2.35 (q, 2H)<br>δ 2.45 (br, 4H)<br>δ 4.15 (s, 1H) |
| 5 | 4-Ethylmorpholinedimethyl-aluminum hydride | liquid | colorless | δ −0.48 (s, 6H)<br>δ 0.75 (t, 3H)<br>δ 2.10 (m, 2H)<br>δ 2.13 (p, 4H)<br>δ 3.58 (b, 4H)<br>δ 4.17 (s, 1H) |
| 6 | 1,4-Dimethylpiperazine-dimethylaluminum hydride | solid | colorless | δ −0.55 (s, 3H)<br>δ −0.50 (s, 3H)<br>δ −0.45 (s)<br>δ 1.83 (s, 6H)<br>δ 2.33 (s, 8H)<br>δ 4.05 (br) |

EXAMPLE 7

Preparation of 1-Methylpiperidinedimethylaluminum hydride in Solution of 1-Methylpiperidine To 80 g of the liquid compound, 1-methylpiperidinedimethylaluminum hydride, from Example 3, were added 20 g of purified 1-methylpiperidine was added to yield a colorless solution.

EXAMPLE 8

Among the compounds of the invention, 1-methylpyrrolidinedimethylaluminum hydride prepared according to Example 1, 1-ethylpiperidinedimethylaluminum hydride prepared according to Example 4, and the 1-methylpiperidinedimethylaluminum hydride solution prepared according to Example 7 were tested for aluminum film vapor deposition by the is following procedure.

Test 1

The compounds synthesized in Example 1 and Example 4, 1-methylpyrrolidinedimethylaluminum hydride and 1-ethylpiperidinedimathylaluminum hydride, respectively, were each added to a stainless steel bubbler, and then heated to 40° to 50° C. Argon or nitrogen gas was used as the carrier gas by bubbling through the solution at a flow rate of 100–600 SCCM (standard cubic centimeters per minute or cm$^3$/minute).

The vaporized precursor compound was diluted by reducing hydrogen gas and passed through a stainless steel tube heated to 40° to 60° C. and into a reactor containing a substrate for film vapor deposition.

The walls of the reactor were heated to 40° to 60° C. to prevent condensation of the precursor. The substrates used were 2,000 Angstrom thick SiO$_2$ with a vapor deposited 900 Angstrom thick TiN (titanium nitride) layer. The substrates were heated at 200° to 300° C. for the vapor deposition of a high purity aluminum film. The vapor deposited aluminum film was measured for the impurity content by Auger electron spectroscopy ("AES") and it was confirmed that the vapor deposited aluminum film was high purity. The sheet resistance was measured by a 4-point probe. The vapor deposition conditions and the analytical data are listed in Table 2.

TABLE 2

| Precursor: | 1-Methylpyrrolidine-dimethyl-aluminum hydride | 1-Ethylpiperidine-dimethyl-aluminum hydride |
|---|---|---|
| Deposition Condition | | |
| Carrier Gas | Nitrogen | Argon |
| Reacting Gas | Hydrogen | Hydrogen |
| Bubbler Temperature (° C.) | 40–50 | 40–50 |
| Reactor Temperature (° C.) | 40–60 | 40–60 |
| Substrate Temperature (° C.) | 200–300 | 200–300 |
| Flow rate (SCCM) | 100–600 | 100–600 |
| Reactor Pressure (torr) | 0.1–6 | 0.1–6 |
| Thin Film | | |
| Deposition Rate (Å/min) | 1000–10,000 | 1000–10,000 |
| Resistivity ($\mu$ohm-cm) | 2.8–3.5 | 2.8–3.5 |
| Impurity | None (by AES) | None (by AES) |
| Adhesion | Excellent on Titanium nitride | Excellent on Titanium nitride |
| Surface Reflectivity | Good | Good |

Test 2

The precursor compound solution prepared according to the procedure of Example 7 was used to form an aluminum film by chemical vapor deposition method. The silicon substrate was the same as the one used in Test 1 and the substrate temperature was 200° to 300° C. The reactor vessel, a glass tube having 5 cm inside diameter and 30 cm length, had one closed end and the open end was connected to a vacuum pump (10$^{-2}$ torr). The precursor solution was filled in a 2 milliliter ("mL") glass container and the glass container was placed in the closed end of the reactor. Several thin silicon pieces were placed in the reactor. The precursor solution and the substrate were maintained at 45° C. and 200° to 300° C., respectively, using independent heating wires. While heating the solution and the substrates, the reactor was evacuated by vacuum pump to $10^{-2}$ torr to obtain a vapor deposited high purity aluminum film. The vapor deposited film was tested by Auger electron spectroscopy ("AES") and 4-point is probe testing. The results, which confirmed that the aluminum film was high purity, are listed in Table 3. This further shows that the invention solution is suitable for direct liquid injector and liquid delivery system as the liquid precursor delivery system.

TABLE 3

| Precursor: | 1-Methylpiperidinedimethyl-aluminum hydride dissolved in 1-Methylpiperidine |
|---|---|
| Deposition Condition | |
| Reacting Gas | Hydrogen |
| Evaporation Temperature (° C.) | 45 |
| Substrate Temperature (° C.) | 200–300 |
| Reactor Pressure (torr) | 0.1–1 |
| Thin Film | |
| Resistivity (μohm-cm) | 2.5–3.2 |
| Impurity | None (by AES) |
| Adhesion | Excellent on Titanium nitride |
| Deposition Rate (Å/min) | 1000–10,000 |

The compounds of the invention can be vapor deposited to form thin films at a wide range of substrate temperature, namely 200° to 300° C. Also, the deposition rate of aluminum film on a silicon substrate, resistivity, impurity level, adhesion strength, and reflectance are superior to those obtained using known precursors. Moreover, the precursors of the invention can be used in direct liquid injector or liquid delivery system in the vapor deposition process, which is an advantage.

What is claimed is:

1. A process for aluminum film formation comprising the step of vapor depositing an aluminum film on a substrate, wherein the source of aluminum in the aluminum film is a vapor deposition precursor comprising an organometallic compound of the formula $H(R')_2Al:L_n$; wherein R' is an alkyl or perfluoroalkyl group having 1 to 4 carbons; and L is a Lewis base capable of providing an unshared electron pair to the aluminum and is selected from thiophene, thiopyran or an organic amine of formula II or III

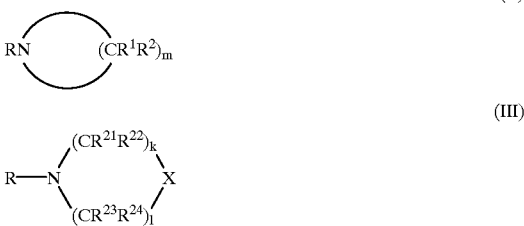

wherein
  R is an alkyl having a carbon number of 1 to 4;
  $R^1$, $R^2$, $R^{21}$, $R^{22}$, $R^{23}$ and $R^{24}$ are each independently hydrogen or an alkyl group having carbon numbers of 1 to 2;
  X is oxygen or an alkyl group containing nitrogen;
  m is an integer from 2 to 8;
  k and l are each independently integers from 1 to 3; and
  n is 1 or 2.

2. The process of claim 1, wherein the organometallic compound is vaporized by thermal energy, plasma or a bias applied on the substrate.

3. The process of claim 1 wherein the organic amine is one or more selected from alkylaziridine, alkylazetidine, alkylpyrrolidine, alkylpiperidine, alkylhexamethyleneimine, alkylheptamethyleneimine, alkylmorpholine, or alkyipiperazine.

4. The process of claim 3 wherein the organic amine is one or more selected from 1,2-dimethylpyrrolidine, 1-methylpyrrolidine, 1-butylpyrrolidine, 1-methylpiperidine, 1-ethylpiperidine, 1,2,2,6,6-pentamethylpiperidine, 4-methylmorpholine, 4-ethylmorpholine or 1,4-dimethylpiperazine.

5. The process of claim 1 wherein the vapor deposition precursor further comprises a heterocyclic amine solvent.

6. The process of claim 5 wherein the heterocyclic amine solvent is one or more selected from 1-methylpyrrolidine, 1-butylpyrrolidine, 1-methylpiperidine, 1-ethylpiperidine, 4-methylmorpholine, 4-ethylmorphoine, or 1,4-dimethylpiperazine.

* * * * *